United States Patent [19]

Dorr et al.

[11] Patent Number: 5,198,988
[45] Date of Patent: Mar. 30, 1993

[54] METHOD OF DETERMINING OPTIMUM OPERATING CONDITIONS IN AN ELECTROCHEMICAL DETECTOR AND ELECTROCHEMICAL DETECTOR USING THE METHOD

[75] Inventors: Thomas Dorr; Clemens Linowski, both of Walbronn, Fed. Rep. of Germany

[73] Assignee: Hewlett-Packard Company, Palo Alto, Calif.

[21] Appl. No.: 568,091

[22] Filed: Aug. 16, 1990

[30] Foreign Application Priority Data

Sep. 15, 1989 [EP] European Pat. Off. .......... 8911 7071

[51] Int. Cl.$^5$ .................. G06F 15/20; C25B 15/02; C25B 15/08
[52] U.S. Cl. .................. 364/497; 73/23.36; 73/23.4; 204/228; 204/231
[58] Field of Search .................. 73/23.36, 23.4; 204/228, 231; 364/497

[56] References Cited

U.S. PATENT DOCUMENTS

| | | | |
|---|---|---|---|
| 4,628,463 | 12/1986 | Sturrock et al. | 364/497 |
| 4,663,006 | 5/1987 | Yao et al. | 204/231 X |
| 4,787,048 | 11/1988 | Freeman et al. | 364/466 |
| 4,846,950 | 7/1989 | Yao et al. | 204/231 X |

FOREIGN PATENT DOCUMENTS

| | | |
|---|---|---|
| 1227244 | 9/1987 | Canada . |
| 01402186 | 5/1985 | European Pat. Off. . |
| 2054169A | 2/1981 | United Kingdom .. |

OTHER PUBLICATIONS

Kheifets, L. Y., et al., Industrial laboratory, 1977, 43:6, 755-757.
McKubre et al.: "Electronic Instrumentation for Electrochemical Studies"; Plenum 1984 pp. 1-98.

Primary Examiner—Edward R. Cosimano

[57] ABSTRACT

A method of determining optimum operating potential in an electrochemical detector and an electrochemical detector for performing the method, particularly for use in connection with a liquid chromatograph, are disclosed. A control and data processing unit causes a plurality of different potentials to be successively applied in an electrochemical cell and a subsequent electrochemical detection of the sample to be performed at each of the potentials. After each adjustment of a new potential, the current behavior at the working electrode in the electrochemical cell is monitored by an amperometer. When the current behavior has stabilized, a trigger signal is produced by the unit which effects an injection of the sample into the separation column of the chromatograph. From the current signals at the working electrode obtained for the different potentials, it can be determined which potential gives optimum detectability of the sample.

8 Claims, 6 Drawing Sheets

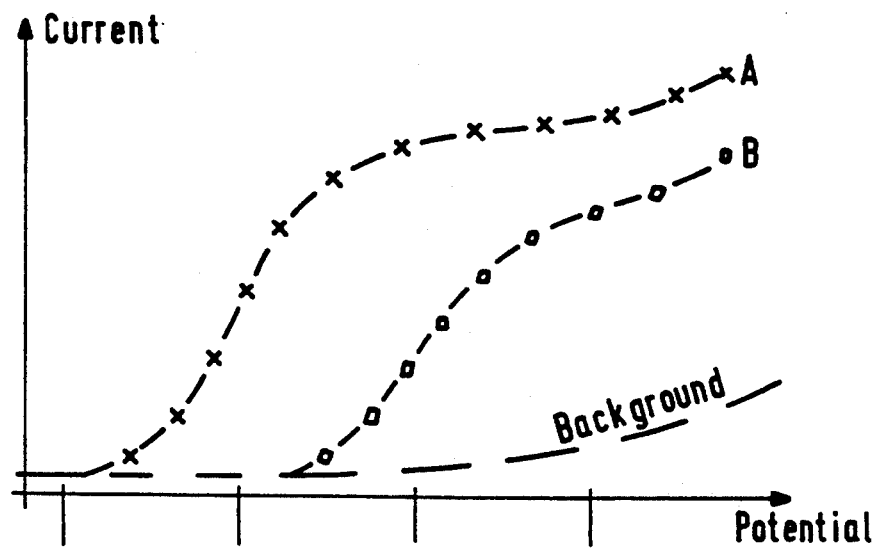
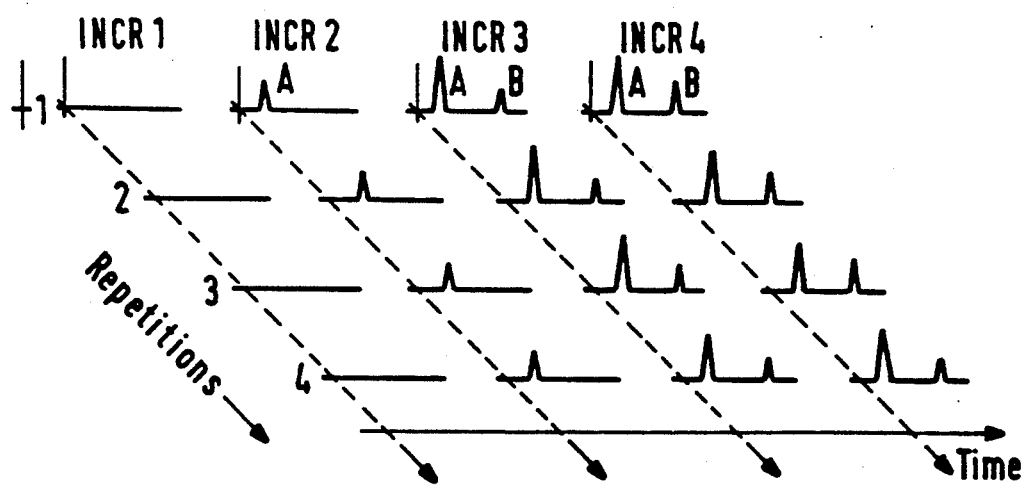
Fig. 4

METHOD OF DETERMINING OPTIMUM OPERATING CONDITIONS IN AN ELECTROCHEMICAL DETECTOR AND ELECTROCHEMICAL DETECTOR USING THE METHOD

BACKGROUND OF THE INVENTION

The invention relates to a method of determining optimum operating conditions in an electrochemical detector and an electrochemical detector using the method. Electrochemical detectors are used for detecting electroactive substances, i.e., substances which are either oxidizable or reducible. Such detectors belong to the most sensitive and most specific detectors presently available and are of particular advantage in liquid chromatography where they are used to detect the liquid eluting from the separation column.

An electrochemical detector is known, for example, from EP-A-140286. This known electrochemical detector comprises an electrochemical cell into which the liquid to be analysed is introduced and in which three electrodes are arranged: a working electrode, a counter electrode (also denoted as auxiliary electrode), and a reference electrode. The electrochemical process is made to occur at the working electrode and the reference electrode compensates for any change in the conductivity of the mobile phase transporting the substances to be analysed. The potential near the counter electrode is held at a fixed value by a control circuit commonly denoted as "potentiostat". The potential near the counter electrode is sensed by the reference electrode which is connected to the potentiostat. When a substance to be analysed arrives at the surface of the working electrode, a current is developed which is converted by an electrometer to a voltage output which can then be processed by further circuitry.

The current developed at the working electrode for a specific electroactive substance in the electrochemical cell varies with the potential applied across the cell. Generally, the current tends to increase when the voltage is increased. Unfortunately, however, unwanted back-ground currents also increase with the voltage. The sensitivity of the electrochemical detector would be the higher the higher the current measured at the working electrode is, but the increased background at higher voltages has a negative effect on the detector sensitivity. It is thus necessary to find a value of the potential which results in optimum detector performance. In addition to the desire for high sensitivity, it is also desirable that the operating potential is such that slight variations of this potential do not cause substantial changes in the current at the working electrode.

A known way to find optimum operating conditions is to record a "cyclovoltamogram" which is a plot of current at the working electrode versus potential. The cyclovoltamogram is produced by sweeping the potential from an initial value to a final value and sweeping it back again to the initial value with simultaneous recording of the current. The time required for recording the cyclovoltamogram typically is less than a minute. The resulting curve has a comparatively complicated shape; in particular, the branch of the curve corresponding to the forward sweep does not coincide with branch corresponding to the backward sweep. From the behavior of the cyclovoltamogram, an experienced operator can obtain an indication at which potential he can expect good detection conditions. The method has the advantage that it can be performed within a short time interval, but the interpretation of the cyclovoltamogram requires a lot of experience and can therefore only be used by well-trained operators. Another shortcoming of this method is its not always satisfactory sensitivity, caused by the comparatively high signal band width which it requires. Another constraint arising when the electrochemical detector is used in connection with a liquid chromatograph, is the difficulty to interpret chromatograms while doing the potential sweep.

SUMMARY OF THE INVENTION

Relative to this prior art, it is an object of the invention to provide a method of determining optimum operating conditions in an electrochemical detector and a corresponding electrochemical detector which permits a reliable determination of such optimum conditions without requiring special knowledge of the operator.

This object is solved by the features of the invention as claimed herein.

According to an underlying principle of the invention, there is not performed a continuous potential sweep as it is done with cyclovoltamograms, but the potential is varied in steps within a predetermined range, whereby after the adjustment of a new potential value the sample is electrochemically detected at this potential, but only if it has been established that the working electrode current has reached a substantially constant level. This is important because electrochemical detectors have long transient times after any parameter changes. In an embodiment of the invention, a fixed wait time is defined after which the current is expected to have stabilized. According to a further, preferred embodiment of the invention, the actual current behavior after the adjustment of a new potential is monitored and a trigger signal is produced when the time variation of the current signal is substantially zero. After the predetermined schedule of potential steps has been executed and the sample has been detected under stable conditions at each of these potentials, it can be taken from the thus obtained set of measuring values which potential is best suited for the detection of the sample.

The invention thus provides for the automatic determination of optimum operating conditions without requiring operator supervision or special knowledge of the operator.

In accordance with an embodiment of the invention, the electrochemical detection of the sample is repeated several times at each adjusted potential value. An advantage of such repetitions is that the resulting electrochemical measuring values are more precise.

The invention is preferably used in connection with a liquid chromatograph wherein a separate injection of the sample into the separation column is made at each of the adjusted potentials in response to the trigger signal indicating that the transient time of the cell is over. When using repetitions, i.e., multiple injections of the sample at a certain potential, the advantage results that from the thus derived plurality of chromatograms information about reproducibility of peak height and area, stability of retention times, sensitivity and background current can be obtained. These parameters cannot be determined in a satisfactory manner with the cyclovoltametric method of the prior art. The invention can also be used when the electrochemical detector is operated in a pulse mode to optimize the potentials of such pulses. Pulse mode operation of an electrochemical detector is known from EP-A 140286, wherein, in addition to a pulsed working potential at which electrochemical detection is performed, oxidizing and reducing pulses are employed to clean passivated working electrodes. In another application of pulse mode, activating pulses of a certain potential are periodically applied to the electrochemical cell to prepare and enable the working electrode for subsequent electrochemical detection at the working potential. The invention can be used to optimize the potentials of the mentioned pulses in addition to the working potential, whereby it is preferred that the different types of potentials are optimized separately. That means, for example, that in a first part of the process only the working potential is incremented to find the optimum working potential, and that in a separate part of the process the cleaning potential is incremented to find the optimum cleaning potential. It is understood that the expression "operating potential" in claim 1 is thus not limited to the working potential but also includes the mentioned pulse potentials.

BRIEF DESCRIPTION OF THE DRAWINGS

Subsequently, an embodiment of the invention is explained with reference to the drawings.

FIG. 4 is a plot of working electrode current versus applied potential for two sample components A and B obtained according to the method of the invention, below which are corresponding chromatograms obtained at four different potentials for four successive injections.

FIGS. 5a-d are graphical representations for illustrating the generation of a trigger signal in response to which a new liquid chromatographic injection is carried out after an increment of the potential in the cell, wherein FIGS. 5a and 5b are plots of working electrode current versus time, and FIGS. 5c and 5d show the time derivative of the curve in FIG. 5b.

In FIG. 6, step 101 is the addition of electroactive sample to the electrochemical detector, step 102 is the application of a plurality of potentials to the cell, step 103 is the creation of a stabilized current for each potential, step 104 is producing a trigger signal for each stabilized current, step 105 is the electrochemical detection of the sample in response to each trigger signal, and step 106 is the determination of optimum potential from detection results.

DETAILED DESCRIPTION OF THE INVENTION

Figure 1:
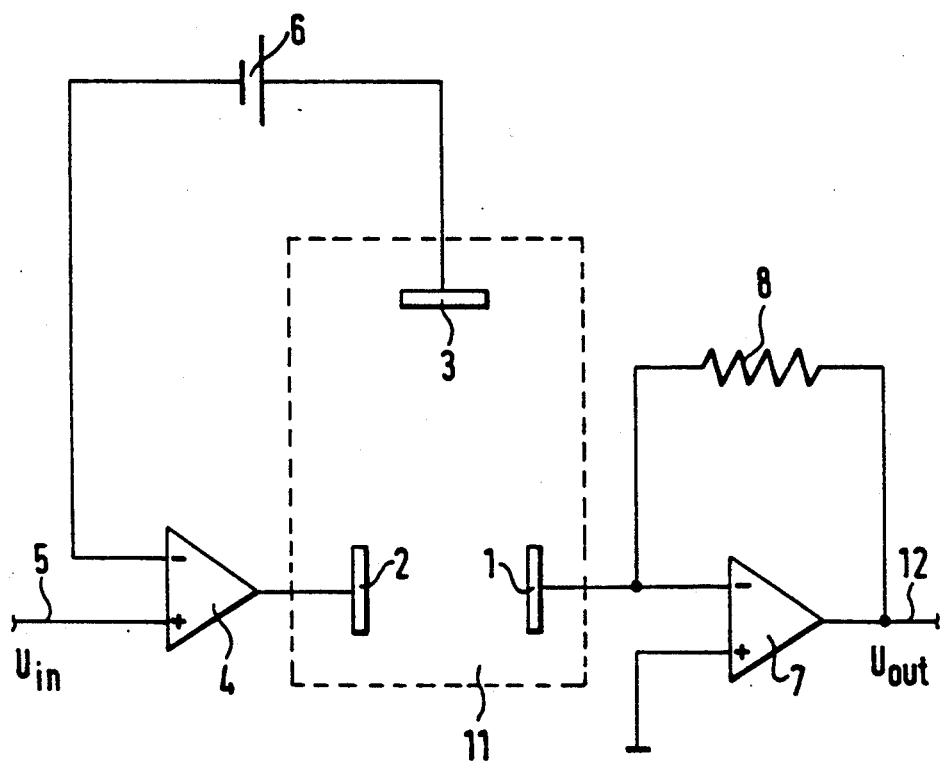
FIG. 1 is a schematic diagram of the basic components of an electrochemical detector.

FIG. 1 schematically shows some basic components of an electrochemical detector: A working electrode 1, a counter electrode or auxiliary electrode 2, and a reference electrode 3 are arranged in a electrochemical cell 11 into which the liquid to be analysed is introduced. The cell may be of any type, such as a flow-through cell into which the effluent of a liquid chromatographic separation column is introduced or a cell wherein the liquid to be analysed is stagnant. Also, the electrochemical cell may be a thin-layer cell, a wall jet cell, or a coulometric cell.

The auxiliary electrode 2 is connected to the output of an operational amplifier 4. The positive input of operational amplifier 4 is connected to a line 5 on which an input voltage Uin can be applied. The inverting input of operational amplifier 4 is connected to the reference electrode 3. Operational amplifier 4 is operated in the voltage follower mode, with the reference electrode serving as a probe to feedback information on the potential of the liquid in the cell for comparison with the applied value Uin. This arrangement with operational amplifier 4 which serves to maintain a constant potential difference between the liquid in the cell and the working electrode is commonly called "potentiostat".

The working electrode 1 is connected to the inverting input of an operational amplifier 7. The non-inverting input of operational amplifier 7 is connected to ground and a resistor 8 is arranged in the feedback loop of the operational amplifier 7. This circuitry functions as a current-to-voltage converter which provides an output voltage $U_{out}$ on a line 12 which is proportional to the current received from the working electrode 1 and to the resistance value of resistor 8. The arrangement of operational amplifier 7 and resistor 8 is also referred to as "amperometer". Alternative electronic designs to the one described for performing the amperometer function are disclosed, for example, in: M.C. McKubre, D.D. MacDonald "Electronic instrumentation for electrochemical studies", Plenum 1984.

The reference electrode 3 can be of any known type, for example a metal which is immersed in a solution of its salts, such as a silver wire immersed in a solution of silver chloride (AgCl) as described in the above mentioned prior art EP-A-140286, having a well-defined concentration of chlorine ions. In FIG. 1, the redox couple constituting the reference electrode is indicated at reference numeral 6. The reference electrode may have an internal electrolyte coupled to the eluent in the electrochemical cell via an "ion bridge" such as a membrane or porous material; alternatively, in particular in connection with a liquid chromatograph, the electrolyte can be provided by the mobile phase passing through the electrochemical cell 11.

Figure 2:
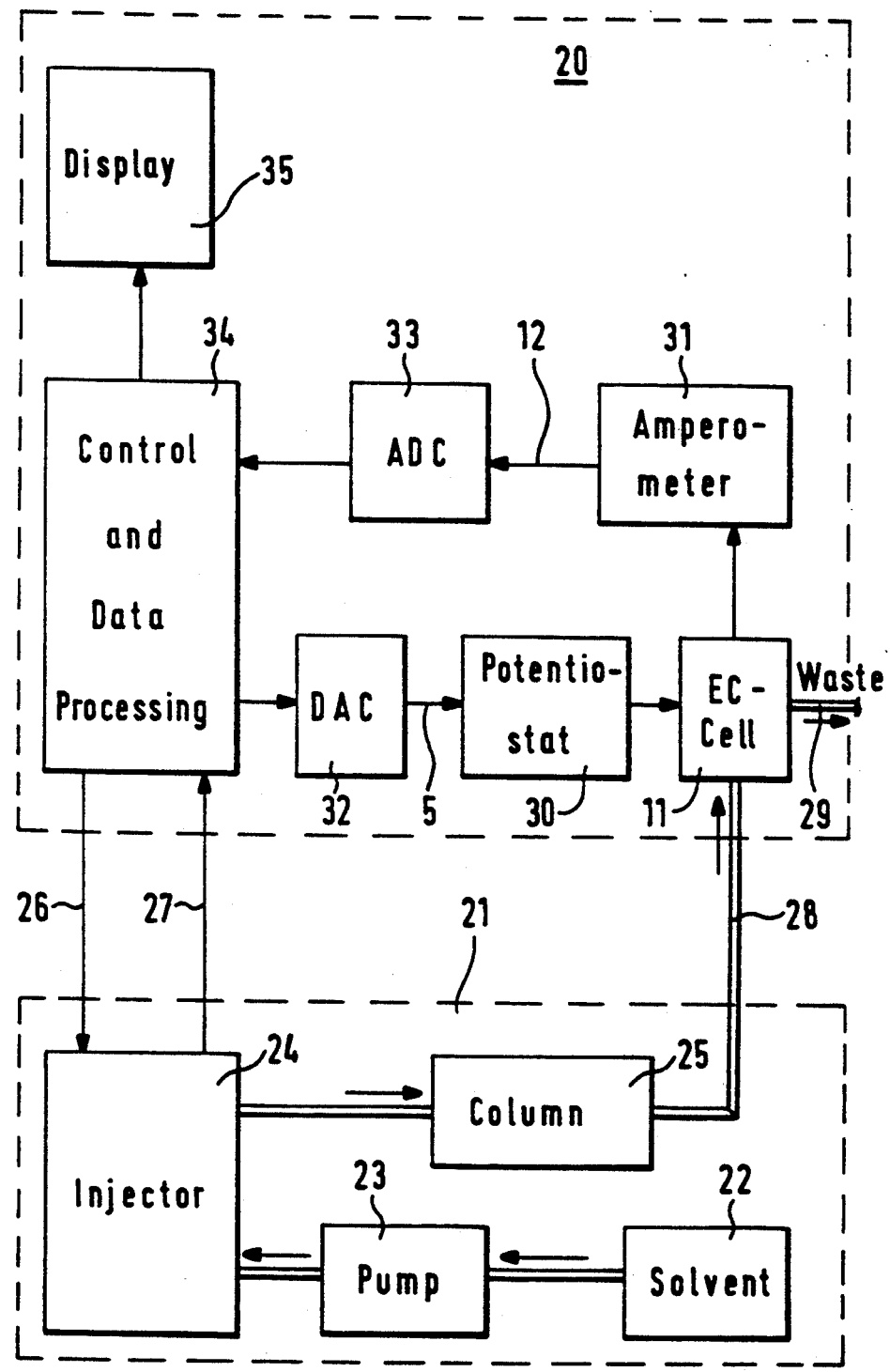
FIG. 2 is a schematic diagram of an electrochemical detector of the invention coupled to a liquid chromatograph.

FIG. 2 schematically shows an electrochemical detector according to the invention comprising the components described in connection with FIG. 1 as well as a liquid chromatograph coupled to the detector such that it can detect substances leaving the separation column of the chromatograph. The portions of FIG. 2 relating to the electro chemical detector are indicated by block 20, and those relating to the chromatograph by block 21.

The liquid chromatograph comprises a solvent source 22, a pump 23 for pressurizing the solvent, a sample injector 24 for introducing the substances to be analysed into the high pressure solvent stream and a separation column 25 from which different substances elute at different times. The injector 24 is controlled by the electrochemical detector via control lines 26, 27 in a way to be explained in more detail below so that injection occurs only at points in time determined by the detector.

The outlet of the separation column 25 is connected to the electro chemical cell 11 of the detector via a suitable tube 28. The electro chemical cell comprises an outlet tube 29 through which liquid is removed from the cell. A potentiostat 30 and an amperometer 31 of the type shown in FIG. 1 or comparable other ones (see above) are coupled to the electrochemical cell 11. The output signal of the amperometer 31 is supplied on line 12 (see also FIG. 1) to an analog to digital converter 33 which provides at its output a digital signal corresponding to the output signal Uout of the amperometer 31. This digital signal is supplied to a control and data processing unit 34 where it can be stored and further processed. The unit 34 preferably comprises a microprocessor for processing data and for generating control signals under control of a program. The digitized values can be displayed on a display means 35, preferably as a plot of detector signal (current at the working electrode) versus time. The resulting plot is a chromatogram, typically comprising several peaks which correspond to the different sample components which have been separated by the column 25.

In the following, an embodiment of the method of the invention for use in connection with a liquid chromatograph as shown in FIG. 2 is described in more detail. In a first step of the method of the invention, illustrated in FIG. 3a, an initial potential Pot1 is applied to the electrochemical cell 11 under control of the control and data processing unit 34 via a digital to analog converter 32 and potentiostat 30. The initial value Pot1 can be selected by a user or can be determined by unit 34. When the potential in the electrochemical cell has been set to the value Pot1, the current at the working electrode shows the behavior illustrated in FIG. 3b, i.e., the current curve sharply drops and then reaches a portion where it is substantially flat. When this flat portion has been reached, i.e., when the current has stabilized after the adjustment of the new potential, a "ready" signal on line 26 is supplied to the injector 24 of the liquid chromatograph. In response to the "ready" signal, the sample to be chromatographically analysed is injected, then separated in the column 25 and finally electrochemically detected in the cell 11. The current signal caused by a sample component is digitized by A/D converter 33 and processed and stored in unit 34. A line 27 serves to transmit information that an injection with subsequent electrochemical detection has been completed.

As a result of such an injection, a chromatogram of the sample is produced which is stored in unit 34. The chromatogram can be displayed on display means 35. The injection of the sample can be repeated several times at the potential Pot1. The chromatograms resulting from these injections can either all be displayed separately or they can be added by the unit 34 to produce a chromatogram which corresponds to an average value for the different injections. By performing several injections, the signal-to-noise ratio of the chromatogram is improved. Furthermore, it is possible to determine the standard deviations of the chromatographic peak heights and areas and of the retention times at a certain potential when multiple injections are made at this potential. These standard deviations are important criteria for the chromatographer in assessing the quality of the chromatographic conditions.

Figure 3A:
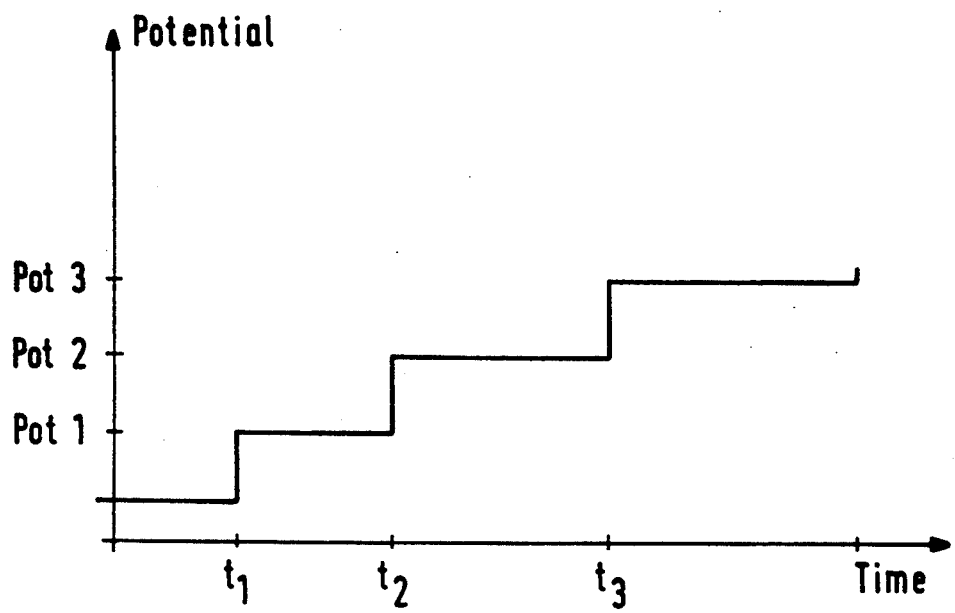
FIG. 3a is a plot of applied potential in the electrochemical cell versus time to illustrate the voltage increments used in the method of the invention.

When the injections at potential Pot1 have been completed, a new potential Pot2 is applied at time t2 as shown in FIG. 3a. Again, it is delayed the current in the cell does no longer change substantially before an injection of the sample is started. Then, the same procedure as at potential Pot2 is performed. At time t3, a new potential Pot3 is adjusted and the previously described steps are performed. In FIG. 3a, the potential increments (Pot1-Pot2, Pot2-Pot3) are equal, but it is understood that the increments could follow any predetermined sequence of values. According to a practical example, the potential increments are in the order of 100 mV. The stepwise increase of the potential is stopped when a predetermined final value is reached. The information gathered at the various adjusted potentials is displayed or printed out and the user thus has the possibility to derive therefrom at which potential he can expect optimum detection conditions. The electrodetection of the sample may be repeated several times at each adjusted potential value.

Figure 3B:
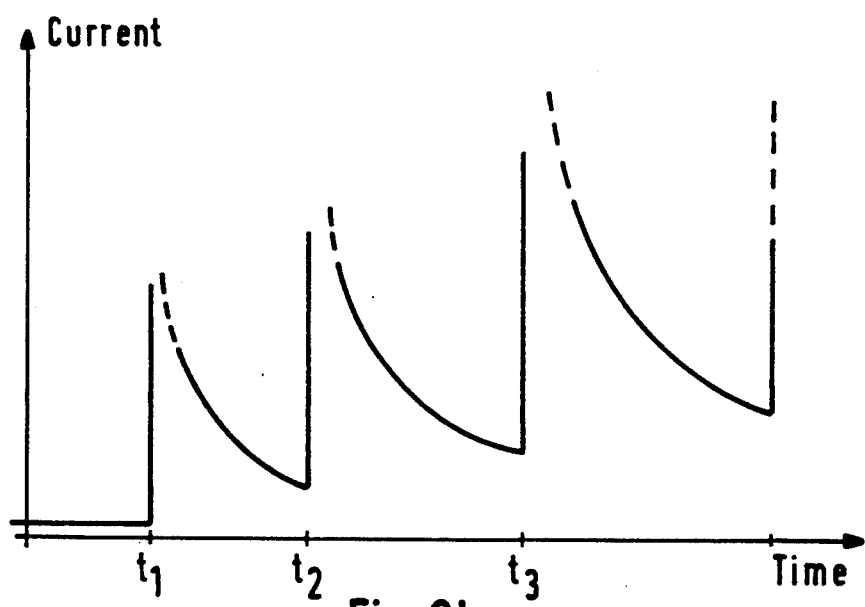
FIG. 3b is a plot of the working electrode current versus time resulting when the potentials according to FIG. 3a are applied.

In the embodiment shown in FIGS. 3a, 3b, the time intervals between successive potential increments, i.e., the time intervals (t1,t2) and (t2,t3) are not equal. This is due to the fact that in this embodiment the time interval between the adjustment of a new potential and the time when the "ready" signal is generated is made dependent on the actually measured current curves (FIG. 3b), respectively. Since the current curves are different for different potentials (see FIG. 3b), this time interval changes. Further details how the "ready" signal is derived from the measured current curves are explained below with reference to FIG. 5a-d. In an alternative embodiment, a fixed wait time between the adjustment of a new potential and the generation of the "ready" signal can be defined. Such a fixed wait time, however, is not satisfactory in all respects, because it may occur, particularly at higher potentials, that the current has not yet stabilized completely when the "ready" signal is generated. If, on the other hand, the wait time is selected to be very large, the total procedure becomes time consuming. Consequently, a variable wait time according to the first mentioned alternative is preferred.

FIG. 4 shows a typical result of the just described procedure of potential incrementing. The graphical representation in the upper half is a plot of working electrode current versus applied potential for two sample components A and B, respectively. Stated in other words, the curves reflect the peak values for a specific component in a chromatogram obtained at the respective potential. The plot also indicates the unwanted background signal in the electrochemical cell. The curves A and B have a qualitatively similar behavior, i.e., they have a flat start portion at the left, a steep portion in the middle followed by a plateau-like portion which finally increases again with a higher background. Generally, good operating conditions of the electrochemical detector can be expected in the plateau-like portion. As can be seen from the drawing, the position of the plateau can vary for different components so that the user, in determining the preferred operating potential, generally has to find a compromise between the various sample components he is interested in.

An additional help to the user in selecting the optimum potential can be to display the actually derived chromatograms at the different adjusted potentials. Such a display is shown in the lower half of FIG. 4 in a perspective view. The horizontal axis again is the time axis along which four potential increments labelled with INCR 1, . . . , INCR 4 are represented. At each of the four potentials, four injections of the sample are performed resulting in four chromatograms which are arranged along the axis labelled "repetitions". At INCR 1, there are no chromatographic peaks to be observed at all four injections. At INCR 2, only the component A is observed. The corresponding peak in the chromatogram is labelled "A". At INCR 3, both components A and B appear at the four injections. At INCR 4, the two components A and B again appear at all four injections. If the sample has a greater number of components, the resulting chromatograms will of course have a correspondingly higher number of peaks. The representation shown in the lower half of FIG. 4 allows the user to quickly identify the potential at which the best signal-to-noise behavior and separation quality (characterized by parameters like peak purity, reproducibility, peak height and area) will result. Instead of displaying all the chromatograms resulting at a certain potential, it is also possible to combine them into a single one and to display only this combined chromatogram.

Electrochemical measuring arrangements are very sensitive to any parameter changes such as variations in the flow of liquid through the electrochemical cell or variations of the potential, and have a long transient time after any parameter changes or disturbances. As shown in FIG. 3b, the working electrode current also has such a transient behavior and it is important that the electrochemical detection of the sample is only carried out when the current has reached a comparatively constant level after the potential has been incremented. According to a preferred embodiment of the invention, a drift trigger is provided which is operative to enable the injection of the sample and electrochemical detection only if the current actually has become stable. This embodiment is now described with reference to FIGS. 5a–d.

Figure 5:
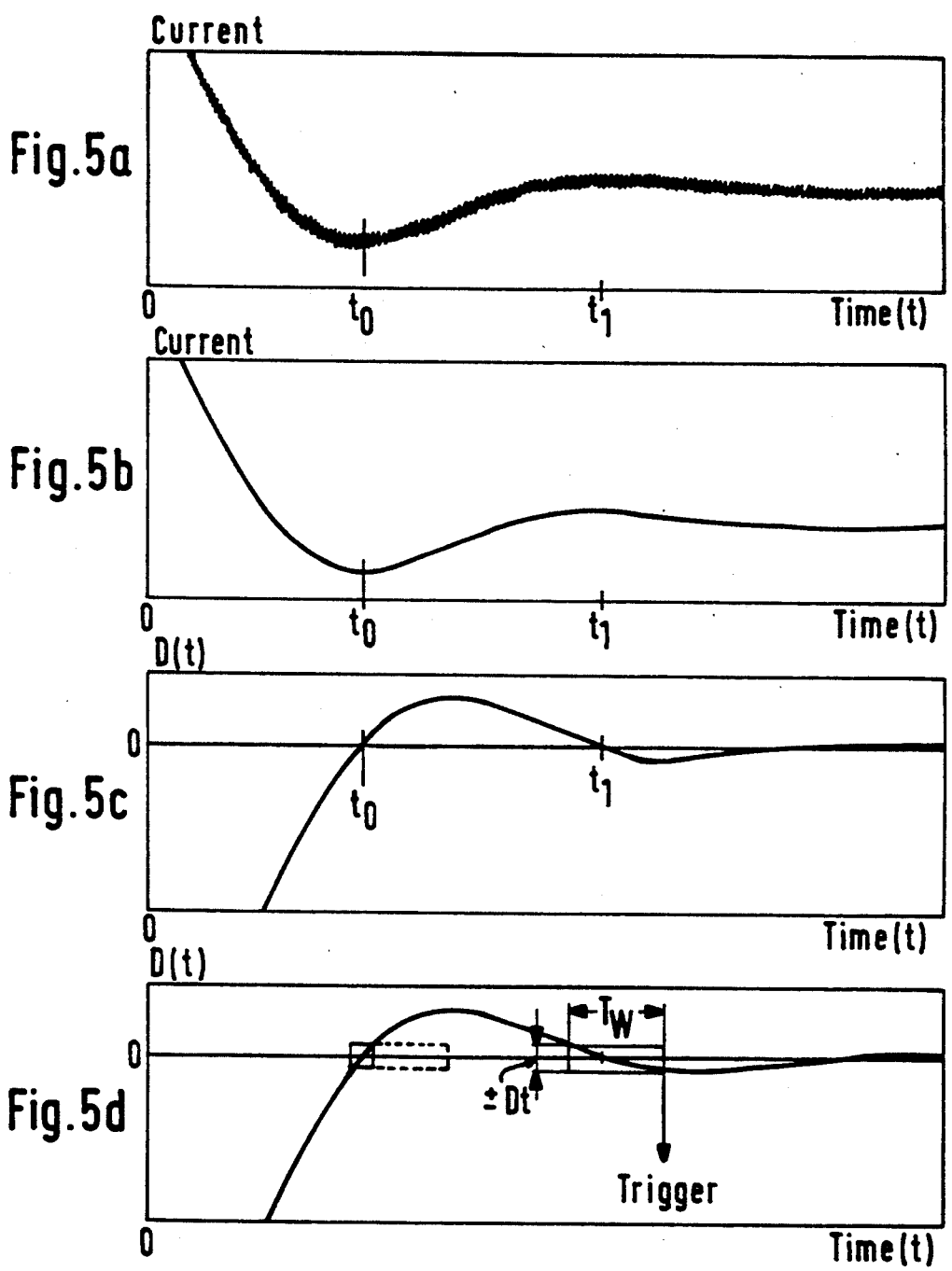
Figure 6:
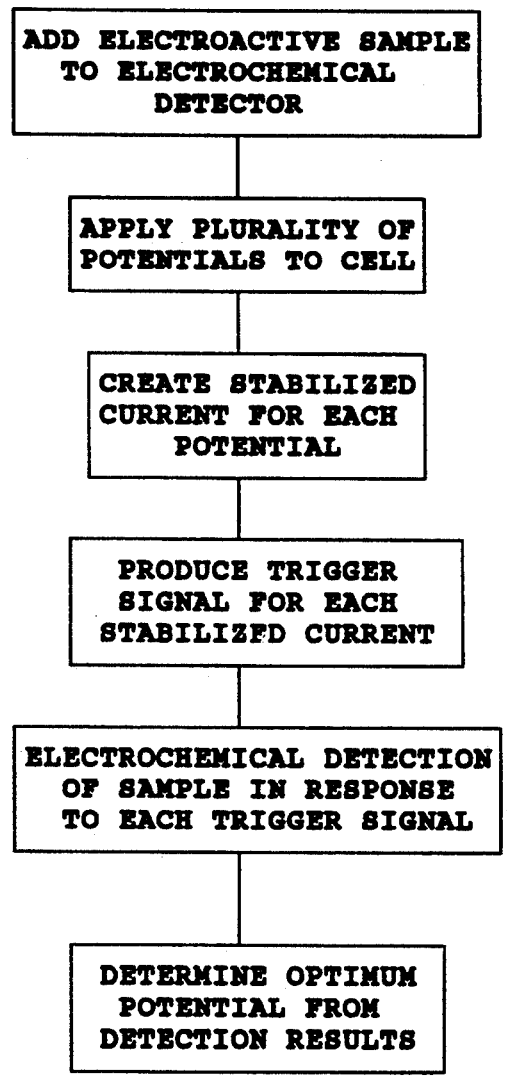
FIG. 6 is a flow sheet of the method described in claim 1 and described in detail hereinafter.

FIG. 5a shows a typical curve of the working electrode current as a function of time after the potential has been incremented (t=0). It can be seen that the curve comprises some noise. In a first data processing step, performed by data processing unit 34, the noise is reduced by conventional noise suppression methods such as digital filtering. The resulting curve is shown in FIG. 5b. In the next step, the time derivative of the curve of FIG. 5b is generated. The resulting curve D(t) is shown in FIG. 5c. The curve D(t) has zero passages where the original curve (FIG. 5b) has a maximum or a minimum, for example at $t_0$ and $t_1$. As can be seen from FIG. 5b, the point $t_0$ does not yet correspond to stable conditions, since the current is rising again after $t_0$. It is therefore necessary to further examine the curve of FIG. 5c.

The different behavior at points $t_0$ and $t_1$ can be classified with a window function as illustrated in FIG. 5d. First, a window having a height of 2 $D_t$, i.e. an elongation of $D_t$ along the vertical axis in the positive and in the negative direction, and a duration $T_w$ is defined. This window is arranged symmetrically around the zero passages $t_0$ and $t_1$. Only if the curve D(t) remains within the limits $+D_t$ and $-D_t$ during the time $T_w$, a trigger signal is produced which indicates that stable conditions have been reached. At time $t_0$, for example, the curve D(t) remains within the limits $+D_t$, $-D_t$ only for a short predetermined interval indicated by the solid block. The duration of the time interval $T_w$ would be the sum of the solid block and the block of dashed lines. Consequently, the point $t_0$ is not associated with stable conditions and no trigger signal is produced. Near point $t_1$, the curve D(t) remains within the window $T_w$ (symmetrically positioned around $t_1$) so that, at the end of interval $T_w$, a trigger signal is produced indicating that the current in the electrochemical cell has stabilized and that a new injection can take place.

The window function described above can be implemented by a program being executed in the control and data processing unit 34. The values of $D_t$ and $T_w$ can be stored as fixed values in unit 34. In an alternative embodiment, the user can select these values so that he can use his own criteria when the conditions of the cell are considered stable enough to start an analysis. It has been found in experiments that values of $D_t=1$ nA/min and $T_w=15$ s give good results.

It is also possible to use the instantaneous value of the working electrode current (FIG. 5a, b) as an additional parameter in the generation of the trigger signal. For example, the generation of a trigger signal can be inhibited as long as the current is above a predetermined value. In that way, it is avoided that an electrochemical analysis is performed when the background current is higher than a predetermined value.

In summary, the above described embodiment of the method according to the invention for use in connection with a liquid chromatograph comprises the following steps: First, an initial value of the potential in the electrochemical cell is adjusted, then the working electrode current is monitored and from the time derivative of the current curve, a trigger signal is produced indicating that the current is substantially constant. In response to this trigger signal, an injection of the sample to be analysed into the separation column of the liquid chromatograph is made and the working electrode currents resulting from the sample components are measured. The injections at this potential setting can be repeated several times in order to reduce any noise in the signal and/or to check chromatographic reproducibility of peak heights and areas and retention times. Thereafter, a new potential is adjusted and a new injection of the sample takes place once the trigger signal has been produced indicating that the conditions in the electrochemical cell are substantially stable. Again the working electrode currents corresponding to the sample components of interest are measured. The potential increments with subsequent current measurement are repeated until a final value of the potential is reached. From the measuring values obtained during this systematic potential variation, the operator directly gets the information which potential will give optimum results for his separation problem.

The potential steps can be equidistant or follow any other predetermined schedule. For example, it would also be possible to perform potential decrements from an initial potential to a lower final potential. The foregoing embodiment of the invention has been described in connection with liquid chromatographic separations, but it is understood that the invention can also be used in connection with other analytical separation methods.

In accordance with the foregoing embodiment, the invention is preferably used in determining optimum working electrode potential, but in applications where the electrochemical detector is operated in a pulsed mode wherein cleaning pulses are applied between working electrode pulses in order to reduce electrode contamination (see EP-A-140286), it could also be used to optimize (in addition to the working potential) the potential of such cleaning pulses. The effectiveness of such cleaning pulses can be assessed from the working electrode signal, i.e., the effectiveness is low when the current at the working electrode for a certain working potential is low.

We claim:

1. In a method of determining optimum operating conditions in an electrochemical detector coupled to the outlet of the separation column of a liquid chromatograph for separating a sample to be analyzed into sample components to be detected, which comprises introducing liquid including an electroactive sample component to be detected into a electrochemical cell of the detector and applying a potential between the liquid in the cell and a working electrode, such that a current is created and stabilized at the working electrode, the steps of:

a) successively applying and adjusting a plurality of potentials in the cell with the values of said potentials corresponding to a sequence of discrete values ranging from an initial to final value,
   b) stabilizing said current created at said working electrode with each adjustment of a new potential value, producing a trigger signal indicative of each stabilized current created, which trigger signal triggers the injection of said sample to be analyzed into said separation column, and electrochemically detecting the sample component to be detected in response to each said trigger signal, and
   c) determining from each of said plurality of potentials the optimum operating potential to produce the measuring values with best signal-to-noise behavior for detection of the sample from the sample electrochemical detection results obtained according to step b).

2. A method as in claim 1 wherein the electrochemical detection of the sample in step b is repeated several times at each adjusted potential value.

3. A method as in claim 1, wherein the trigger signal is produced a predetermined time interval after the adjustment of a new potential value.

4. An electrochemical detector for detecting electroactive samples, which detector is coupled to the outlet of the separation column of a liquid chromatograph for separating a sample to be analyzed into sample components to be detected, comprising:

an electrochemical cell for receiving liquid including the sample component to be detected,
   a working electrode,
   means for applying a potential in the cell between the liquid in the cell and the working electrode,
   means for measuring the current created at the working electrode by the sample component to be detected, in combination with control and data processing means coupled to the means for applying a potential in the cell and coupled to the means for measuring the current created at the working electrode, said control and data processing means being operative to:
   successively applying a plurality of potentials in the cell, the values of said plurality of potentials corresponding to a sequence of discrete values ranging from a initial to a final value,
   stabilize said current created at said working electrode after each adjustment of a new potential value,
   produce a trigger signal indicative of each stabilized current, which trigger signal triggers the injection of said sample to be analyzed into said separation column, and
   cause electrochemical detection of the sample component to be detected in response to each trigger signal to enable determination of the optimum detection potential from said plurality of potentials to produce the measuring values with best signal-to-noise behavior.

5. An electrochemical detector as in claim 4, wherein the trigger signal is produced a predetermined time interval after the adjustment of a new potential value.

6. An electrochemical detector as in claim 4, wherein the trigger signal is derived from the curve representing the time behavior of the working electrode current after the adjustment of a new potential.

7. In a method of determining optimum operating conditions in an electrochemical detector which comprises introducing liquid including an electroactive sample to be detected into a electrochemical cell of the detector and applying a potential between the liquid in the cell and a working electrode, such that a current is created and stabilized at the working electrode, the steps of:

a) successively applying and adjusting a plurality of potentials in the cell with the values of said potentials corresponding to a sequence of discrete values ranging from an initial to final value,
   b) stabilizing said current created at said working electrode with each adjustment of a new potential value, producing a trigger signal indicative of each stabilized current created, and electrochemically detecting the sample in response to each said trigger signal, said trigger signal being derived from a curve representing the time behavior of the working electrode current after adjustment of a new potential, and
   c) determining from each of said plurality of potentials the optimum operating potential to produce the measuring values with best signal-to-noise behavior for detection of the sample from the sample electrochemical detection results obtained according to step b).

8. A method as in claim 7, wherein the trigger signal is produced when a zero passage ($t_1$) of the time derivative ($D(t)$) of the curve representing the time behavior of the working electrode current has occurred, and the values of the function ($D(t)$) around the zero passage ($t_1$) have remained within a predetermined interval ($-D_t, +D_t$) for at least a predetermined time $T_w$.

* * * * *